United States Patent
Kuiper et al.

(10) Patent No.: US 11,076,946 B2
(45) Date of Patent: Aug. 3, 2021

(54) FLEXIBLE BARRIER LAYER INCLUDING SUPERELASTIC ALLOYS

(71) Applicant: Verily Life Sciences LLC, Mountain View, CA (US)

(72) Inventors: Stein Kuiper, Pacifica, CA (US); Daniel B. Otts, Pleasanton, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 415 days.

(21) Appl. No.: 16/176,884

(22) Filed: Oct. 31, 2018

(65) Prior Publication Data

US 2019/0142575 A1 May 16, 2019

Related U.S. Application Data

(60) Provisional application No. 62/587,279, filed on Nov. 16, 2017.

(51) Int. Cl.
- *A61F 2/16* (2006.01)
- *G02C 7/08* (2006.01)
- *B29D 11/00* (2006.01)

(52) U.S. Cl.
CPC ......... *A61F 2/1624* (2013.01); *A61F 2/1627* (2013.01); *A61F 2/1648* (2013.01); *B29D 11/00807* (2013.01); *G02C 7/081* (2013.01); A61F 2002/1681 (2013.01); A61F 2210/0014 (2013.01); A61F 2210/0076 (2013.01); A61F 2250/0001 (2013.01); A61F 2250/0002 (2013.01); A61F 2250/0043 (2013.01); B32B 2307/726 (2013.01); G02C 2202/16 (2013.01)

(58) Field of Classification Search
CPC .... A61F 2/1624; A61F 2/1627; A61F 2/1648; A61F 2002/1681; A61F 2210/0014; A61F 2210/0076; A61F 2250/001; A61F 2250/0002; A61F 2250/0043; B29D 11/00807; G02C 7/081; G02C 2202/16; B32B 2307/726

See application file for complete search history.

(56) References Cited

U.S. PATENT DOCUMENTS

| | | |
|---|---|---|
| 9,463,610 B2 | 10/2016 | Tsotsis |
| 9,554,890 B2 | 1/2017 | Wortz et al. |
| 9,715,130 B2 | 7/2017 | Otts et al. |

(Continued)

FOREIGN PATENT DOCUMENTS

CN 105514456 A 4/2016

OTHER PUBLICATIONS

International Search Report and Written Opinion from the International Searching Authority dated Feb. 12, 2019 for International Application No. PCT/US2018/059686, filed Nov. 7, 2018, 13 pages.

(Continued)

*Primary Examiner* — Jennifer Dieterle
*Assistant Examiner* — Tiffany P Shipmon
(74) *Attorney, Agent, or Firm* — Christensen O'Connor Johnson Kindness PLLC

(57) ABSTRACT

An ophthalmic apparatus includes a support structure; a substrate included with the support structure; at least one conductor disposed on the substrate; and a hermetic barrier structure disposed over the at least one conductor. The hermetic barrier structure further includes a stack of alternating flexible insulating material and superelastic metal alloy layers.

21 Claims, 4 Drawing Sheets

(56) References Cited

U.S. PATENT DOCUMENTS

| | | |
|---|---|---|
| 2009/0228101 A1 | 9/2009 | Zadno-Azizi |
| 2011/0219764 A1 | 9/2011 | Anthony et al. |
| 2012/0235277 A1 | 9/2012 | Pugh et al. |
| 2014/0099475 A1 | 4/2014 | Rawlings |
| 2014/0148899 A1 | 5/2014 | Fehr et al. |
| 2015/0133878 A1 | 5/2015 | de Juan, Jr. et al. |
| 2015/0323811 A1 | 11/2015 | Flitsch et al. |
| 2016/0022471 A1 | 1/2016 | Fuglister |
| 2016/0113760 A1 | 4/2016 | Conrad |
| 2017/0165051 A1 | 6/2017 | Mattes et al. |

OTHER PUBLICATIONS

Chinese Office Action, dated Jan. 29, 2021, in corresponding Chinese Patent Application No. 201880073884.X, 6 pages.
Indian Examination Report, dated Mar. 25, 2021, in corresponding Indian Patent Application No. 202047018930, 6 pages.

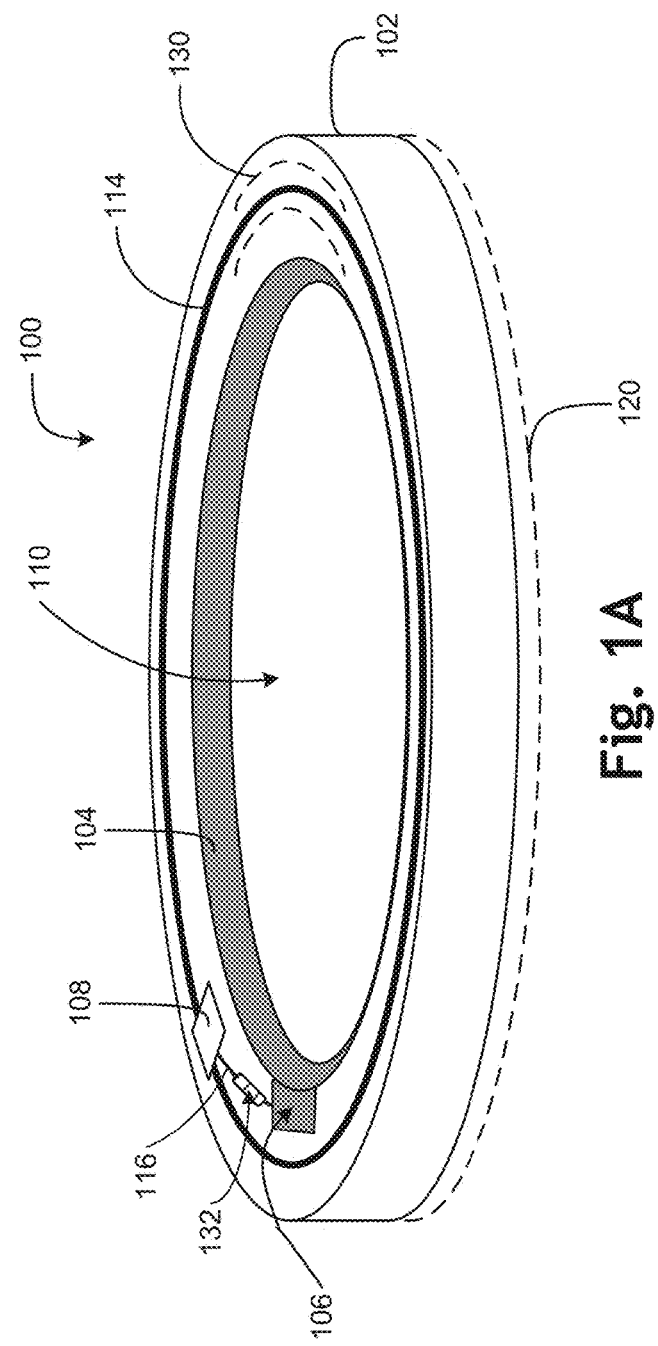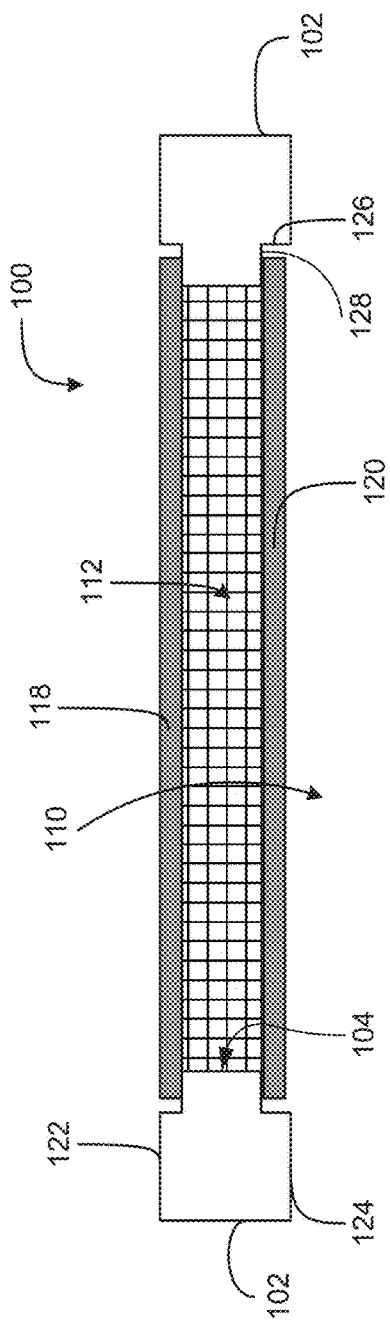
Fig. 1A
Fig. 1B

FLEXIBLE BARRIER LAYER INCLUDING SUPERELASTIC ALLOYS

CROSS-REFERENCE TO RELATED APPLICATION

This application claims the benefit of U.S. Provisional Application No. 62/587,279, filed Nov. 16, 2017, which is hereby incorporated by reference in its entirety.

TECHNICAL FIELD

This disclosure relates generally to ophthalmic devices, and in particular but not exclusively, relates to ophthalmic devices that include hermetic barrier structures.

BACKGROUND INFORMATION

Presbyopia treatment may include implantation of a replacement lens. Such lenses, which may also be referred to as intraocular lenses, may provide static or dynamic accommodation, or a combination thereof. Various techniques may be available to provide dynamic accommodation, such as mechanical or electrical controlled accommodation. The accommodation may be provided by actuation of a dynamic optical component that provides multiple levels of optical power. The change in optical power may provide different focal distances to the user via the intraocular lens. The amount of actuation, however, may depend on the technique used, e.g., mechanical or electrical.

If electrical actuation is used, the electronics and conductors may need to meet certain requirements that relate to visibility, implantation compatibility, and the implantation procedures. For example, it may be desirable to have some or all of the electronics and/or conductors to be elastic, and further formed from materials amenable to use in or on the eye. Additionally, the liquid environment of the eye may impose additional desired qualities to protect the charge carrying components of the conductors, such as a hermetic seal. However, conventional hermetic barriers may not be amenable to being rolled and/or folded. As such, a hermetic barrier that withstands rolling and bending without the generation of defects may be desirable.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

FIGS. 1A and 1B are a perspective and a cross-sectional illustration of an intraocular lens including a hermetic barrier layer formed over one or more conductors in accordance with an embodiment of the disclosure.

DETAILED DESCRIPTION

Figure 2:
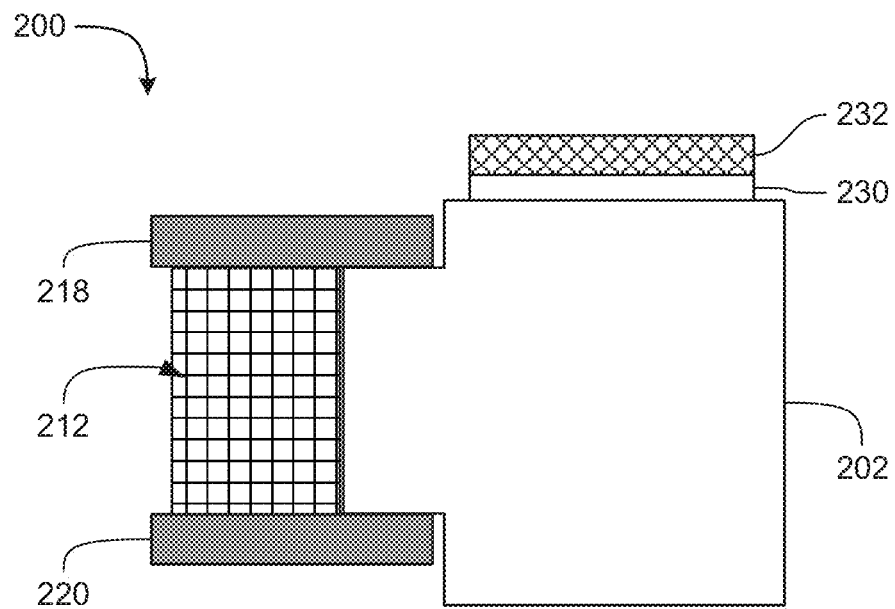
FIG. 2 is a cross-sectional illustration of a portion of an intraocular lens including a hermetic barrier structure disposed over a conductor in accordance with an embodiment of the present disclosure.

Embodiments of an apparatus and method for an intraocular lens having a hermetic barrier formed over one or more conductors are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

An intraocular lens (IOL) may be implanted in a user's eye to assist in accommodation when the user's lens is no longer able to change focus, for example. The IOL may have static optical power or may have the ability to dynamically accommodate, e.g., alter the optical power of the IOL, so the user may change focus similar to the natural eye. To provide dynamic accommodation, the IOL may include electronics, conductive traces, electrodes, and the like, coupled to a dynamic optic located in an optical path of the IOL. The electronics may provide a voltage to the dynamic optic via one or more conductors to cause accommodation, for example.

Additionally, because the IOL will be implanted into the eye, a small incision in the eye may be desirable. Yet, because the IOL may be of the same size as the original lens, for example, a large incision may be required. However, if the IOL is capable of being rolled up into a cylindrical shape or folded, a smaller incision may be possible. In general, most of the materials forming the IOL are amenable to being rolled or folded, but conventional conductors may experience reliability issues due to the stresses of rolling/flexing events. For example, conventional conductors may delaminate from a substrate and/or crack and/or buckle from the stresses induced from rolling. Accordingly, it may be desirable for conductors to be flexible and deformable, e.g., elastic, and further desirable for the conductors to return to a desired shape upon unrolling/unfolding without experiencing inelastic deformation.

Further, because the IOL is located in the liquid environment of the eye, it may be desirable to provide hermetic barriers for protection of the conductors from moisture, ionic content, and/or gases of the eye. The hermetic protection may desirably protect the conductors from degradation due to the moisture, ionic content, and gases. Hermetically sealing the conductors may also prevent detrimental reactions of the eye liquid due to voltages of the conductors, such as electrolysis. And because the IOL may be rolled or bent during insertion, the hermetic barrier may desirably be flexible and stretchable without incurring defects, such as cracks or breaks that could lead to exposure of the underlying conductor. As such, it may be desirable to include a flexible and stretchable hermetic barrier structure over a flexible and stretchable conductor.

It should be noted that while this discussion is centered on IOLs, such discussion is not intended to be limiting, and the aspects of the disclosure are equally applicable to on-eye wearable ophthalmic devices to give at least one example. In general, the features of the disclosure are directed toward elastic and stretchable hermetic barriers and conductors for devices that may experience bending and/or rolling that may damage conventional inelastic hermetic barriers, for example.

FIGS. 1A and 1B are a perspective and a cross-sectional illustration of an IOL 100 including a hermetic barrier layer formed over one or more conductors in accordance with an embodiment of the disclosure. The illustrative embodiment of the IOL 100 includes a support structure 102, a contact pad 106, control electronics 108, a dynamic optic 112, an antenna 114, a conductor 116, a substrate 130, and optical windows 118 and 120. While not shown, the IOL 100 may be enclosed in a transparent or semitransparent biocompatible material. In some embodiments, the IOL 100 will provide dynamic accommodation to a user based on electrowetting technology. In other embodiments, the IOL 100 will provide dynamic accommodation to a user based on liquid crystal technology. Of course, other lensing techniques are also possible. In either embodiment, conductors that interconnect the various electronic components of the IOL 100 may have a hermetic barrier layer formed over them to prevent or reduce the chance of moisture and ionic content from contacting the conductors. The conductors may be interconnects, electrical traces, leads, or any conductive connection/coupling that carries a voltage and/or current. Further, the hermetic barrier may experience rolling and bending events without detrimental cracks and/or kinks forming therein.

The support structure 102 may provide a support frame for the various features of the IOL 100. For example, the support structure 102 may provide support for the contact 106, the control electronics 108, the optical window 116, the conductor 116, the antenna 114, the substrate 130, and various other components discussed herein. In some embodiments, however, some of the components, such as the control electronics, 108, the conductor 116, the antenna 114, and the contact 106 may be disposed on the substrate 130, which is included with the support structure 102. In general, the support structure 102 may be formed from a biocompatible material that is amenable to implantation into an eye. Example materials may include silicones, sol-gels, and AcrySof®. Other biocompatible materials, such as biocompatible hydrogel, hydrophobic acrylic, fluorinated polymethacrylate and/or the like, may also be used. The support structure 102 may be a main structural component of the IOL 100 that provides a platform for other IOL 100 components. The support structure 102 may be flexibly capable of being rolled up and/or folded so that it may be manipulated into a smaller shape to accommodate insertion into an eye through a small incision, e.g., an incision roughly 2 mm in length. The support structure 102 is preferably highly elastic, so that it will return to its original shape after unfolding.

The control electronics 108 may be coupled to at least provide a voltage to the dynamic optic 112. In the illustrated embodiment of the IOL 100, the support structure 102 is annulus-shaped, e.g., washer-shaped, having an opening 110, e.g., an aperture, formed there through. The opening 110 may provide an optical path for the IOL 100. In some embodiments, the optical windows 118 and 120 are be placed over at least the opening 110 on both a top and bottom of the support structure 102.

The opening 110 may be formed by an inner surface, e.g., a sidewall 104, of the support structure 102. In some embodiments, the sidewall 104 may be at a non-orthogonal angle, e.g., an oblique angle, to top and/or bottom surfaces 122, 1224 of the support structure 102. For example, the sidewall may be at a 45° angle to at least one of the top or bottom surfaces of the support structure 102. In general, the type of dynamic optic 112 of the IOL 100 may determine a slope or angle of the sidewall 104 with respect to a top or bottom surface 122, 124 of the support structure 102, and other angles other than 45° are within the scope of the present disclosure. For example, if the dynamic optic 112 is based on electrowetting, the sidewall 104 may be at an oblique angle, and may be in the shape of a conical frustum in some embodiments. However, if the dynamic optic 112 is based on liquid crystal technology, then the angle of the sidewall 104 may be orthogonal to the top and bottom surfaces 122, 124 of the support structure 102.

The support structure 102 may further have a recess formed on an inner edge on both the top and bottom surfaces 122, 124, respectively, that encircles the aperture 110. The recesses may provide a surface for mounting and sealing the optical windows 118, 120 to the support structure 102. The recess may be defined by surfaces 126 and 128 formed into the bottom surface 124, which may be mirrored on the top surface 122. In some embodiments, the recess formed into the top surface 122 and the recess formed into the bottom surface 124 may be different and provide different surface areas of the support structure 102. Of course, the support structure 102 may be formed without the surfaces 126 and 128 and the optical windows 118 and 120 may, instead, be disposed on the top and bottom surfaces 122 and 124, respectively.

The conductor 116 and/or the antenna 114 may have a hermetic barrier structure 132 formed over them. In some embodiments, it may be desirable that the conductor 116, antenna 114, and the hermetic barrier 132 be elastic and return to a desired shape upon rolling/unrolling or folding/unfolding of the IOL 100. To obtain such qualities, the conductor 116, the antenna 114, and the hermetic barrier 132 may be formed from materials that may be deformed, rolled up, or have a large degree of flexibility without negatively affecting their electrical and/or mechanical properties upon unrolling, unfolding, etc. For example, the conductor 116 and the antenna 114 may be formed from one or more superelastic alloys, and the hermetic barrier structure 132 may be formed from a stack of alternating flexible insulating material and superelastic alloy layers.

In general, it may be desirable for the materials to withstand a large amount of deformation, e.g., rolling/bending, without resulting in inelastic deformation and/or the formation of kinks and/or cracks. To obtain such characteristics, the materials should have a high yield strain, with a minimum yield strain ranging from 0.25% to 5%, or greater. Example materials for the conductors and superelastic alloys may include spring steel or one or more shape memory alloys. Example materials for the flexible insulating material may include elastomers, polydimethylsiloxane (PDMS) silicone, room temperature vulcanization (RTV) silicone, silicone pressure-sensitive adhesive (PSA), "rubbery" PSAs (e.g., polyisobutylene (PIB) PSA, natural rubbers, polyisoprene rubbers, and block copolymers), or chemical vapor deposition (CVD) silicones. Additional examples may include acrylate, urethanes, methacrylate, and other elastic materials such as polyimide, polyetherimide, polyethylene terephthalate (PET), parylene, acrylic copolymer, and the like. Many of the example materials may have strain yields from 10% to 40%, or more, yet the yield strain of individual layers on the hermetic structure 132 may vary depending on the amount of strain they may experience while in a rolled/folded state. In general, the flexible insulating material should be biocompatible and elastic/stretchable.

The contact pad 106 may electrically couple the control electronics 108 to the dynamic optic 112, and may be disposed on a surface of the support structure 102, or the substrate 130. In some embodiments, the contact pad 106 may be part of an electrode of the dynamic optic 112. However, the contract pad 106 does not need to be part of the electrode, and may be a separate component. Additionally, the contact pad 106 may have a hermetic barrier layer structure 132 disposed over at least a portion of it, but may be (partially) imbedded in the support structure 102 in some embodiments.

The substrate 130 may be formed into an annular shape and sized to encompass the aperture 110. The substrate 130 may further be sized to fit on a top or bottom surface 122, 124 of the support structure 102, or fit within the support structure 102. For example, the substrate 130 may be embedded in the support structure 102. In some embodiments, the support structure material may form a layer of the hermetic barrier structure 132. The substrate may be formed from a biocompatible plastic and may be rigid enough to provide mechanical support to at least the control electronics 108, the antenna 114, the conductor 116, and the hermetic barrier structure 132. In embodiments where the substrate 130 is embedded in the support structure 102, at least the control electronics 108, conductor 116, hermetic barrier 132, and the antenna 114 may also be embedded in the support structure 102. In such an embodiment, and as noted, the material forming the support structure 102 may form a final layer of the hermetic barrier structure 132.

The first and second optical windows 118, 120 may be mounted to top and bottom sides of the support structure 102. The first and second optical windows 118, 120 may be formed from transparent or partially transparent polymerics or thin glass. Example polymerics include Polydimethylsiloxane, hydrophobic acrylic (e.g., AcrySof), of silicones, acrylics, epoxies, urethanes, combinations thereof, and the like. While top and bottom are used herein to discuss the opposite sides of the support structure 102, the top and bottom designations do not notate any directionality to the IOL 100 and are used merely as a reference with respect FIG. 1B.

The optical windows 118, 120 may be transparent and disposed to cover the aperture 110. The optical windows 118, 120 may be with or without optical power. In some embodiments, one or both of the optical windows provides static optical power to the IOL 100, which may be affected by the dynamic accommodation of the IOL 100. In some embodiments, the optical windows 118, 120 do not have any optical power. In either embodiment, the optical windows 118, 120 may be coupled to the support structure 102 to retain the two immiscible fluids within a cavity, where the cavity is formed by the support structure 102 and the optical windows 118, 120.

Additionally, one or both of the optical windows may be conductive. For example, the optical window 118 and/or 120 may be conductive. A transparent conductor, such as indium tin oxide (ITO) may be deposited on the optical windows 118 and/or 120, for example. Having one or both of the optical windows conductive may allow a potential difference to be applied to the dynamic optic 112 for causing changes in accommodation.

As noted, the conductors of the IOL 100, such as the conductor 116 the antenna 114, may be formed from an elastic, superelastic, or pseudoelastic metal alloy. It may be desirable that the metal alloy have a minimum yield strain of 0.25%, although 0.5% is preferred in some embodiments, and 5% or greater is preferred in yet other embodiments. In some embodiments, the conductors may be formed from spring steel, which has a yield strain of 0.25%, or a shape-memory alloy. For example, the shape-memory alloy may be Nitinol (nickel-titanium alloy) of various compositions, which has a yield strain of a 5% or greater, copper-zinc-aluminum, copper-aluminum, copper-aluminum-nickel, or copper-aluminum-beryllium. In other embodiments, it may be desirable to form the conductors out of a biocompatible elastic metal alloy, such as a medical grade titanium having high elasticity. For example, the medical grade titanium may be Ti6Al4V.

Additionally, the IOL 100 may be folded or rolled up for insertion into a user's eye without experiencing inelastic deformation upon unfolding/unrolling. A radius of bending or rolling may also affect the desired thickness of the conductors and the hermetic barrier structure 132. It may be desirable that the conductors not plastically deform after rolling or bending and that they return to a desired shape without any kinks or cracks formed thereon/therein, which may be dependent upon the yield strain of the metal alloy used.

FIG. 2 is a cross-sectional illustration of a portion of an IOL 200 including a hermetic barrier structure disposed over a conductor in accordance with an embodiment of the present disclosure. The IOL 200 may be an example of the IOL 100. The IOL 200 at least includes a support structure 202, a dynamic optic 212, optical windows 218 and 220, substrate 230, conductor 216, hermetic barrier structure 232, and substrate 230. In the illustrated embodiment, the substrate 230 is disposed on a surface of the support structure 202, and the conductor 216 and the hermetic barrier structure 232 are disposed on the substrate 230. The hermetic barrier layer structure 232 may prevent moisture and/or ionic content from reaching the conductor, and may additionally be flexible and stretchable to experience folding/rolling without degradation.

The substrate 230 may provide mechanical support for the various electronics and interconnections of the IOL 200. For example, the substrate 230 may provide mechanical support at least for an antenna, control electronics, and conductors coupling the various electronics such as shown in FIG. 1A. The substrate 230 may be annular shaped and may fit around an aperture of the IOL 200, similar to the aperture 110. The substrate 230 may be formed from a sturdy, yet flexible and bendable plastic. For example, the substrate 230 can be formed from Polyimide. Of course, other plastics may be implemented and contemplated herein.

The hermetic barrier structure 232 may be formed from a plurality of alternating layers of a flexible insulating material and a superelastic alloy. The hermetic barrier structure 232 may be flexible and stretchable to withstand bending and/or rolling without stretching out of shape or forming defects. The flexible insulating material may be any type of known silicone, such as RTV silicone, silicone with a pressure sensitive adhesive (PSA), chemical vapor deposition (CVD)

silicone, "rubbery" PSAs, and the like. The "rubbery" PSAs utilize various rubber bases formulated with tackifiers, antioxidants, and solvents to produce PSA formulations. Additional examples may include acrylate, urethanes, methacrylate, and other elastic materials such as polyimide, polyetherimide, polyethylene terephthalate (PET), parylene, acrylic copolymer, and the like.

In some embodiments, a second hermetic barrier structure 232 may be deposed on an opposing side of the substrate 230. In such an embodiment, the conductor 216 may be hermetically protected from top and bottom.

Figure 3:
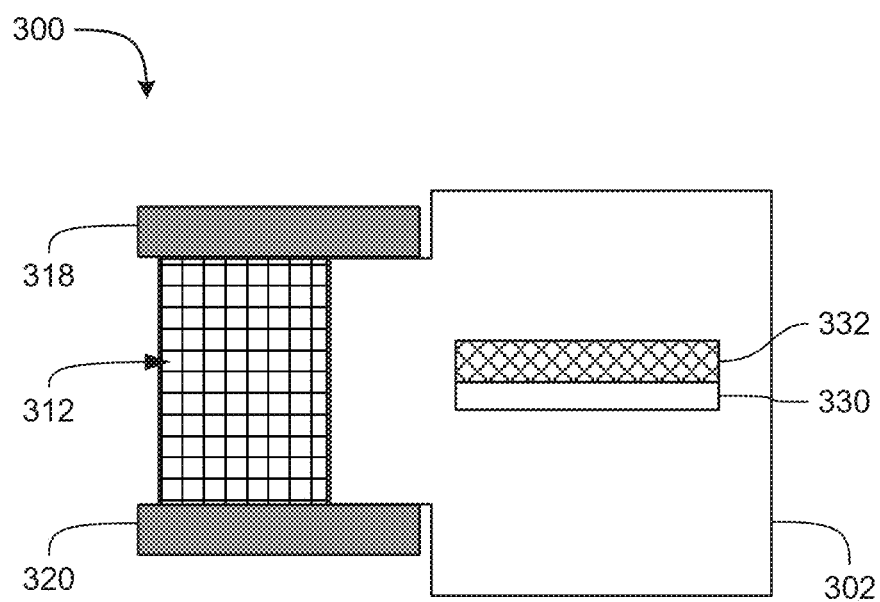
FIG. 3 is a cross-sectional illustration of a partial intraocular lens including a hermetic barrier structure disposed over a conductor in accordance with an embodiment of the disclosure.

FIG. 3 is a cross-sectional illustration of a partial IOL 300 including a hermetic barrier structure disposed over a conductor in accordance with an embodiment of the disclosure. The partial IOL 300 is an example of the IOL 100, and may be similar to the IOL 200. However, the substrate 330 and any electronics and conductors deposed thereon may be embedded in the support structure 302. For example, the substrate 330, conductor 316, and hermetic barrier structure 332 may be imbedded in the support structure 302. In some embodiments, the support structure 302 that covers the hermetic barrier structure 332 may provide a final flexible insulating material layer to the hermetic barrier and may further reduce parasitic capacitance. In some embodiments, a second hermetic barrier structure 332 may be deposed on an opposing side of the substrate 330.

Figure 4:
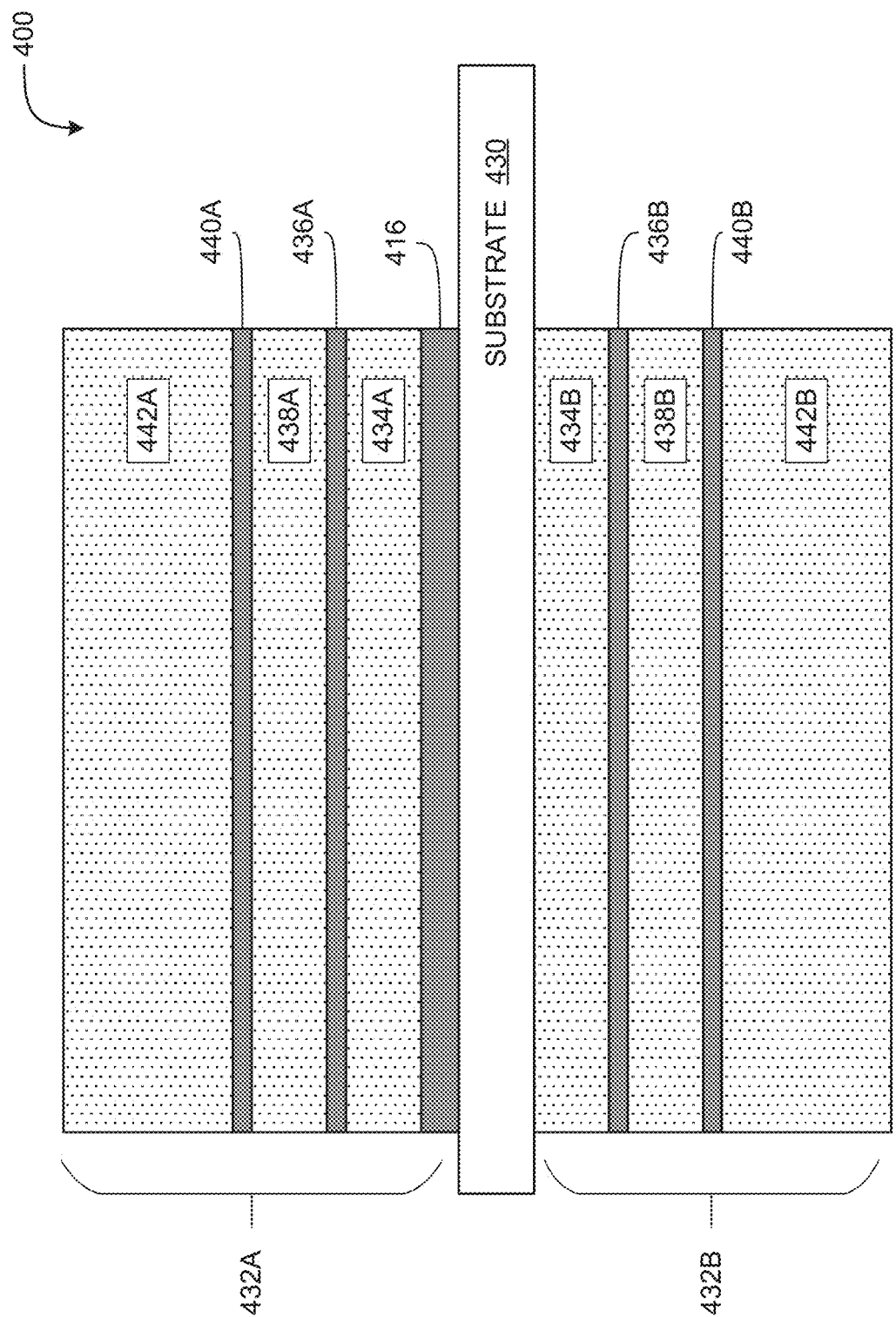
FIG. 4 is an illustrative hermetic barrier structure disposed on a conductor in accordance with an embodiment of the present disclosure.

FIG. 4 is an illustrative hermetic barrier structure 432 disposed on a conductor in accordance with an embodiment of the present disclosure. The hermetic barrier structure 432 may be an example of the hermetic barrier structures 132, 232, and/or 332. The hermetic barrier structure 432 may provide a barrier to moisture, ionic component, and possibly gas while being flexible and stretchable. Stretching the hermetic barrier structure 432 may not induce defects or inelastic defamation.

The hermetic barrier structure 432 may be formed over a conductor 416, which is disposed on a substrate 430. The conductor 416 and the substrate 430 may be examples of the conductors 116, 216 and/or 316, and the substrates 130, 230, and/or 330, respectively. The conductor 416 may be formed from a superelastic alloy, such as Nitinol, but other materials as discussed above may also be implemented. Forming the conductor 430 out of a superelastic alloy may ensure that the conductor 430 does not degrade due to bending or rolling. Further, forming the conductor 430 out of the superelastic alloy may allow it to deform similar to the rest of the hermetic barrier structure 432 so to reduce or prevent delamination. A thickness of the conductor 416 may be dependent upon a desired sheet resistance, and may be from 1 micron to 10 micron. In some embodiments, the conductor 416 may be 5 microns in thickness.

In some embodiments, the hermetic barrier structure 432 may include two structures, such as 432A and 432B. However, in some embodiments, the hermetic barrier structure 432 may only include a single structure 432A disposed over the conductor 430. Including both structures 432A on top and 432B on bottom may reduce any parasitic capacitance induced by the conductor 430, and provide a hermetic barrier to at least two sides of the conductor 416.

The hermetic barrier structure 432 may include a plurality of flexible insulating material layers alternating with a plurality of superelastic alloy layers. For example, a first flexible insulating material layer 434A may be directly disposed on the conductor 430. In some embodiments, the first flexible insulating material layer 434A may be around 20 microns thick. A first superelastic alloy layer 436A may be disposed on the first flexible insulating material layer 434A. In some embodiments, the first elastic alloy layer 436A may be around one micron thick. Second flexible insulating material and superelastic alloy layers 438A and 440A, respectively, may be disposed on the first superelastic alloy layer 436A. Similar to the first layers, the second flexible insulating material and superelastic alloy layers 438A and 440A may be 20 and 1 microns thick, respectively. Atop the second superelastic alloy layer 440A, a third flexible insulating material layer 442A may be disposed. The third flexible insulating material layer 442A, however, may be much thicker than the first and second flexible insulating material layers 434A, 438A. For example, the third flexible insulating material layer 442A may be around 150 microns thick. The third flexible insulating material layer 442A may be thicker than the first and second flexible insulating material layers 434A and 438A to lower any parasitic capacitance generated by the combination of the conductor 416 and the barrier layer structure 432A. The hermetic barrier structure 432B may be formed similar to the hermetic barrier structure 432A. As noted, the hermetic barrier structure 432B may be optional.

In embodiments where the combination of the substrate 430, conductor 416, and the hermetic barrier structure 432 are imbedded in a support structure, analogous to the IOL 300, and the thick flexible insulating material layers 442A, B may be formed from the support structure itself. For example, the combination of the substrate 430, conductor 416, and all but the final layers of the hermetic barrier structures 432A, B may be placed in a mold, and the material for the support structure may be injected around the combination to form both the support structure and the layers 442A, B.

While the hermetic barrier structure 432 is shown to include two superelastic alloy layers 436 and 440, and three flexible insulating material layers 434, 438, and 442, such number of layers is a non-limiting aspect of the present disclosure and more or fewer layers may be implemented to form a hermetic barrier structure. Accordingly, the hermetic barrier structure 432 is for example only.

Figure 5:
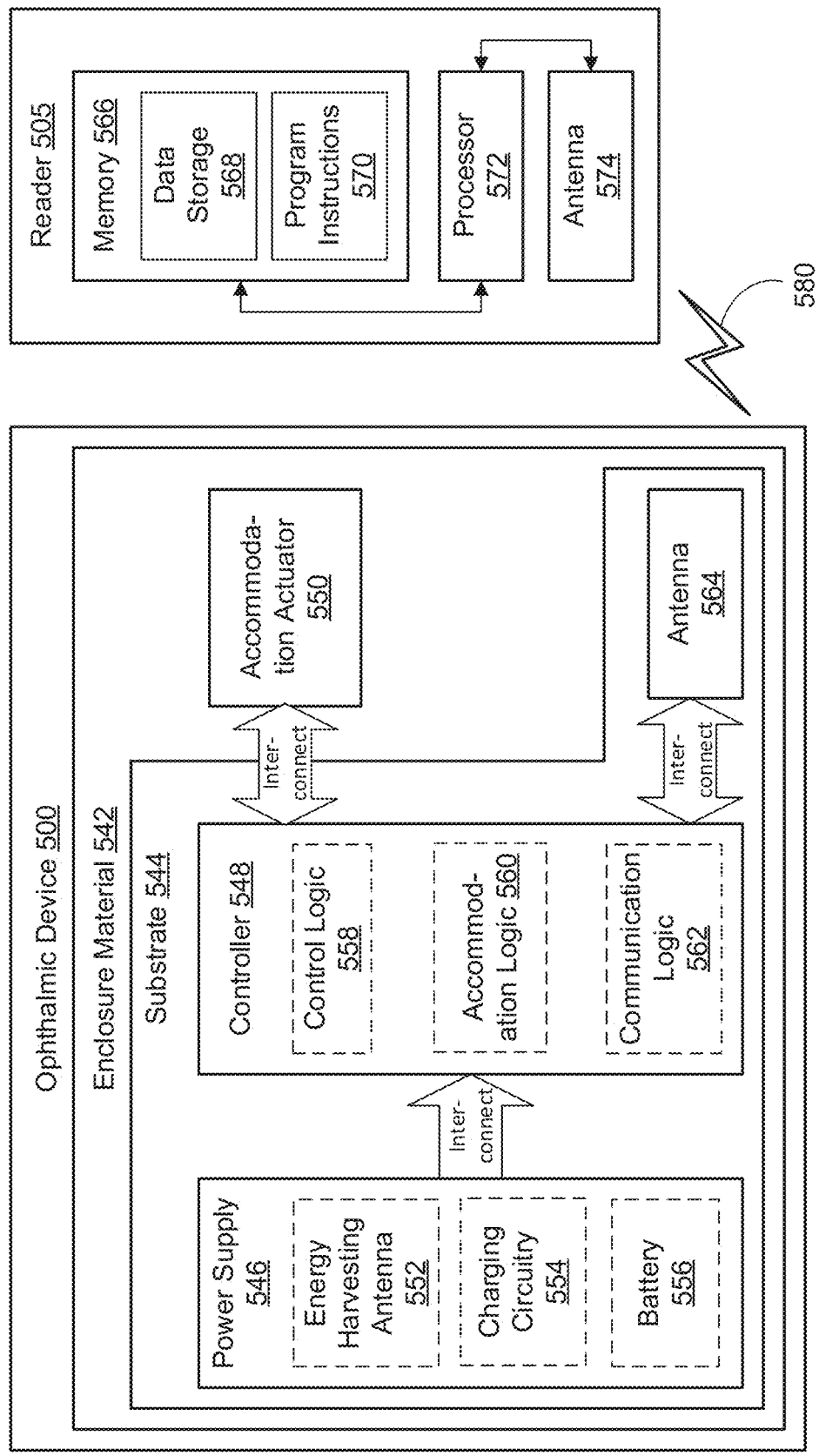
FIG. 5 is a functional block diagram of an ophthalmic device including a hermetic barrier disposed on a conductor in accordance with an embodiment of the present disclosure.

FIG. 5 is a functional block diagram of an ophthalmic device 500 including a hermetic barrier disposed on a conductor in accordance with an embodiment of the present disclosure. Ophthalmic device 500 may be an implantable device, such as an intraocular lens, and may be one example of the IOLs 100, 200 and/or 300. In the depicted embodiment, ophthalmic device 500 includes an enclosure material 542 formed to be implanted into an eye. A substrate 544 is embedded within or surrounded by enclosure material 542 to provide a mounting surface for a power supply 546, a controller 548, an antenna 564, and various interconnects. The substrate 544 and the associated electronics may be one implementation of the control electronics 108 and an associated substrate, such as the substrate 130. In some embodiments, the substrate 544 may be embedded in a support structure, such as the support structure 102, which is embedded in the enclosure material 542. The illustrated embodiment of power supply 546 includes an energy harvesting antenna 552, charging circuitry 554, and a battery 556. The illustrated embodiment of controller 548 includes control logic 558, accommodation logic 560, and communication logic 562. As shown, accommodation actuator 550 is disposed in the enclosure material 542.

Power supply 546 supplies operating voltages to the controller 548 and/or the accommodation actuator 550, which is an example of the dynamic optic 112. Antenna 564 is operated by the controller 548 to communicate information to and/or from ophthalmic device 500. In the illustrated embodiment, antenna 564, controller 548, and power supply 546 are disposed on/in substrate 544, while accommodation actuator 550 is disposed in enclosure material 542, such as in an aperture area of a support structure (not shown) and not in/on substrate 544. However, in other embodiments, the various pieces of circuitry and devices contained in ophthalmic device 500 may be disposed in/on substrate 544 or in enclosure material 542, depending on the specific design of ophthalmic device 500.

Substrate 544 includes one or more surfaces suitable for mounting controller 548, power supply 546, and antenna 564. Substrate 544 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide or silver nanowire mesh) can be patterned on substrate 544 to form circuitry, electrodes, etc. For example, antenna 564 can be formed by depositing a pattern of gold or another conductive material on substrate 544. Similarly, interconnects can be formed by depositing suitable patterns of conductive materials on substrate 544. A combination of resists, masks, and deposition techniques can be employed to pattern materials on substrate 544. Substrate 544 can be a relatively soft material, such as a polymer or another material sufficient to structurally support the circuitry and/or electronics within enclosure material 542 while being flexible enough to being rolled up or folded. Ophthalmic device 500 can alternatively be arranged with a group of unconnected substrates rather than a single substrate 544. For example, controller 548 and power supply 546 can be mounted to one substrate 544, while antenna 564 is mounted to another substrate 544 and the two can be electrically connected via interconnects. Substrate 544 may also be a continuous piece of semiconductor, housing all or some of the aforementioned pieces of device architecture as integrated circuitry.

Substrate 544 can be shaped as a flattened ring with a radial width dimension sufficient to provide a mounting platform for the embedded electronic components. Substrate 544 can have a thickness sufficiently small to allow substrate 544 to be embedded in enclosure material 542 without adversely influencing the profile of ophthalmic device 500. Substrate 544 can have a thickness sufficiently large to provide structural stability suitable for supporting the electronics mounted thereon. For example, substrate 544 can be shaped as a ring with a diameter of about 10 millimeters, a radial width of about 1 millimeter (e.g., an outer radius 1 millimeter larger than an inner radius), and a thickness of about 50 micrometers. In some embodiments, the substrate 544 may encircle at least the optical area associated with the accommodation actuator 550, and may be analogous to the support structures 102 and/or 202. For example, the substrate 544 may be disposed in a peripheral area and in between at least two optical elements, such as optical elements 214 and 216.

Additionally, the power supply 546 may be coupled to the controller 548 via one or more interconnects. Similarly, the controller 548 may be coupled to the accommodation actuator 550 and the antenna 564 via one or more interconnects. The interconnects may be examples of the conductor 116. In some embodiments, the interconnects may be covered by a hermetic barrier structure (not shown) similar to at least the hermetic barrier structure 432.

In the illustrated embodiment, power supply 546 includes a battery 556 to power the various embedded electronics, including controller 548. Battery 556 may be inductively charged by charging circuitry 554 and energy harvesting antenna 552. In one embodiment, antenna 564 and energy harvesting antenna 552 are independent antennae, which serve their respective functions of energy harvesting and communications. In another embodiment, energy harvesting antenna 552 and antenna 564 are the same physical antenna that are time shared for their respective functions of inductive charging and wireless communications with reader 505. Additionally or alternatively, power supply 546 may include a solar cell ("photovoltaic cell") to capture energy from incoming ultraviolet, visible, and/or infrared radiation. Furthermore, an inertial power scavenging system can be included to capture energy from ambient vibrations.

Charging circuitry 554 may include a rectifier/regulator to condition the captured energy for charging battery 556 and/or directly power controller 548. Charging circuitry 554 may also include one or more energy storage devices to mitigate high frequency variations in energy harvesting antenna 552. For example, one or more energy storage devices (e.g., a capacitor, an inductor, etc.) can be connected to function as a low-pass filter.

Controller 548 contains logic to choreograph the operation of the other embedded components. Control logic 558 controls the general operation of ophthalmic device 500, including providing a logical user interface, power control functionality, etc. Accommodation logic 560 includes logic for receiving signals from sensors monitoring the orientation of the eye, determining the current gaze direction or focal distance of the user, and manipulating accommodation actuator 550 (focal distance of the contact lens) in response to these physical cues. The auto-accommodation can be implemented in real-time based upon feedback from gaze tracking, or permit the user to select specific accommodation regimes (e.g., near-field accommodation for reading, far-field accommodation for regular activities, etc.). Communication logic 562 provides communication protocols for wireless communication with reader 505 via antenna 564. In one embodiment, communication logic 562 provides backscatter communication via antenna 564 when in the presence of an electromagnetic field 580 output from reader 505. In one embodiment, communication logic 562 operates as a smart wireless radio-frequency identification ("RFID") tag that modulates the impedance of antenna 564 for backscatter wireless communications. The various logic modules of controller 548 may be implemented in software/firmware executed on a general purpose microprocessor, in hardware (e.g., application specific integrated circuit), or a combination of both.

Ophthalmic device 500 may include various other embedded electronics and logic modules. For example, a light source or pixel array may be included to provide visible feedback to the user. An accelerometer or gyroscope may be included to provide positional, rotational, directional or acceleration feedback information to controller 548.

The illustrated embodiment also includes reader 505 with a processor 572, an antenna 574, and memory 566. Memory 566 in reader 505 includes data storage 568 and program instructions 570. As shown reader 505 may be disposed outside of ophthalmic device 500, but may be placed in its proximity to charge ophthalmic device 500, send instructions to ophthalmic device 500, and/or extract data from ophthalmic device 500. In one embodiment, reader 505 may resemble a conventional contact lens holder that the user places ophthalmic device 500 in at night to charge, extract data, clean the lens, etc.

External reader 505 includes antenna 574 (or group of more than one antenna) to send and receive wireless signals 580 to and from ophthalmic device 500. External reader 505 also includes a computing system with processor 572 in communication with memory 566. Memory 566 is a non-transitory computer-readable medium that can include, without limitation, magnetic disks, optical disks, organic memory, and/or any other volatile (e.g., RAM) or non-volatile (e.g., ROM) storage system readable by the processor 572. Memory 566 can include a data storage 568 to store indications of data, such as data logs (e.g., user logs), program settings (e.g., to adjust behavior of ophthalmic device 500 and/or external reader 505), etc. Memory 566 can also include program instructions 570 for execution by processor 572 to cause the external reader 505 to perform processes specified by the instructions 570. For example, program instructions 570 can cause external reader 505 to provide a user interface that allows for retrieving information communicated from ophthalmic device 500 or allows transmitting information to ophthalmic device 500 to program or otherwise select operational modes of ophthalmic device 500. External reader 505 can also include one or more hardware components for operating antenna 574 to send and receive wireless signals 580 to and from ophthalmic device 500.

External reader 505 can be a smart phone, digital assistant, or other portable computing device with wireless connectivity sufficient to provide the wireless communication link 580. External reader 505 can also be implemented as an antenna module that can be plugged into a portable computing device, such as in an embodiment where the communication link 580 operates at carrier frequencies not commonly employed in portable computing devices. In some instances, external reader 505 is a special-purpose device configured to be worn relatively near a wearer's eye to allow the wireless communication link 580 to operate with a low power budget. For example, the external reader 505 can be integrated in a piece of jewelry such as a necklace, earing, etc. or integrated in an article of clothing worn near the head, such as a hat, headband, etc.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An ophthalmic apparatus comprising:
a support structure;
a substrate included with the support structure;
at least one conductor disposed on the substrate; and
a hermetic barrier structure disposed over the at least one conductor, the hermetic barrier structure including a stack of alternating flexible insulating material and superelastic metal alloy layers.

2. The ophthalmic apparatus of claim 1, wherein the substrate is embedded in the support structure.

3. The ophthalmic apparatus of claim 1, wherein the substrate is disposed on a surface of the support structure.

4. The ophthalmic apparatus of claim 1, wherein the at least one conductor is formed from a superelastic metal alloy.

5. The ophthalmic apparatus of claim 1, wherein the hermetic barrier layer includes:
a first flexible insulating material layer disposed on the at least one conductor;
a first superelastic metal alloy layer disposed on the first flexible insulating material layer;
a second flexible insulating material layer disposed on the first superelastic metal alloy layer;
a second superelastic metal alloy layer disposed on the second flexible insulating material layer; and
a third flexible insulating material layer disposed on the second superelastic metal alloy layer.

6. The ophthalmic apparatus of claim 1, wherein a second hermetic barrier layer is formed on a bottom side of the substrate in an area corresponding to the at least one conductor.

7. The ophthalmic apparatus of claim 1, wherein the superelastic metal alloy is selected from one of Nitinol, copper-zinc-aluminum, copper-aluminum, copper-aluminum-nickel, and copper-aluminum-beryllium.

8. The ophthalmic apparatus of claim 1, wherein the first, second and third flexible insulating material layers are formed from one of silicone, pressure sensitive adhesive (PSA) silicone, rubbery PSAs, polyimide, polyetherimide, polyethylene terephthalate, parylene, or acrylic copolymer.

9. The ophthalmic apparatus of claim 1, wherein the support structure is annular shaped forming an aperture, and wherein the ophthalmic apparatus further comprises:
a dynamic optic arranged in the aperture, and coupled to provide dynamic accommodation in response to a control signal; and
optical windows disposed on opposing sides of the support structure.

10. The ophthalmic apparatus of claim 9, further comprising:
control electronics disposed on the substrate and electrically coupled to control the dynamic optic, wherein the control electronics are coupled to the dynamic optic via the at least one conductor to provide the control signal.

11. The ophthalmic apparatus of claim 1, further comprising an antenna disposed on the substrate.

12. The ophthalmic apparatus of claim 11, wherein a third hermetic barrier layer is disposed on the antenna.

13. An intraocular lens, comprising:
a support structure;
a substrate embedded in the support structure;
at least one conductor disposed on a surface of the substrate, wherein the at least one conductor is formed from a superelastic metal alloy; and
a hermetic barrier structure disposed on the at least one conductor, the hermetic barrier structure formed from a stack of alternating flexible insulating material and superelastic metal alloy layers.

14. The intraocular lens of claim 13, wherein the superelastic metal alloy is a shape-memory alloy.

15. The intraocular lens of claim 14, wherein the shape memory alloy is selected from one of Nitinol, copper-zinc-aluminum, copper-aluminum, copper-aluminum-nickel, and copper-aluminum-beryllium.

16. The intraocular lens of claim 13, wherein a second hermetic barrier layer is formed on a bottom side of the substrate corresponding with the at least one conductor.

17. The intraocular lens of claim 13, wherein each of the flexible insulating material layers are formed from one of silicone, pressure sensitive adhesive (PSA) silicone, rubbery PSAs polyimide, polyetherimide, polyethylene terephthalate, parylene, or acrylic copolymer.

18. The intraocular lens of claim 13, wherein the hermetic barrier layer includes:
   a first flexible insulating material layer disposed on the at least one conductor;
   a first superelastic metal alloy layer disposed on the first flexible insulating material layer;
   a second flexible insulating material layer disposed on the first superelastic metal alloy layer;
   a second superelastic metal alloy layer disposed on the second flexible insulating material layer; and
   a third flexible insulating material layer disposed on the second superelastic metal alloy layer.

19. The intraocular lens of claim 13, wherein the support structure is annular shaped forming an aperture, and wherein the intraocular lens further comprises:
   a dynamic optic arranged in the aperture, and coupled to provide dynamic accommodation in response to a control signal; and
   optical windows disposed on opposing sides of the support structure and spanning across at least the dynamic optic.

20. The intraocular lens of claim 13, further comprising:
   control electronics disposed on the substrate and electrically coupled to control the dynamic optic, wherein the control electronics are coupled to the dynamic optic via the at least on conductor to provide the control signal.

21. The intraocular lens of claim 13, further comprising an antenna disposed on the substrate wherein a third hermetic barrier layer is disposed on the antenna.

* * * * *